United States Patent
Jaschke et al.

(10) Patent No.: US 7,655,750 B2
(45) Date of Patent: Feb. 2, 2010

(54) PROCESS FOR THE CONTINUOUS PREPARATION AND ISOLATION OF SOLUBLE PRECERAMIC OLIGOMERS AND/OR POLYMERS

(75) Inventors: Thomas Jaschke, Stuttgart (DE); Martin Jansen, Leonberg (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 45 days.

(21) Appl. No.: 12/066,367

(22) PCT Filed: Sep. 7, 2006

(86) PCT No.: PCT/EP2006/008745

§ 371 (c)(1),
(2), (4) Date: Mar. 10, 2008

(87) PCT Pub. No.: WO2007/028620

PCT Pub. Date: Mar. 15, 2007

(65) Prior Publication Data

US 2008/0255325 A1    Oct. 16, 2008

(30) Foreign Application Priority Data

Sep. 8, 2005    (DE) .................... 10 2005 042 813

(51) Int. Cl.
*C08F 6/00* (2006.01)
*C08G 77/44* (2006.01)

(52) U.S. Cl. .................. 528/501; 501/88; 501/96.2; 501/93; 501/96.1; 501/96.4; 526/67; 528/5; 528/25; 556/173; 556/389; 556/402

(58) Field of Classification Search .......... 501/88, 501/96.2, 93, 96.1, 96.3, 96.4; 526/67; 528/5, 528/25; 556/173, 389, 402
See application file for complete search history.

(56) References Cited

U.S. PATENT DOCUMENTS

| 7,297,649 | B2 * | 11/2007 | Jansen et al. ............... 501/96.2 |
| 2009/0030157 | A1 * | 1/2009 | Jansen et al. ................ 525/389 |

FOREIGN PATENT DOCUMENTS

| EP | 0502399 A2 | 9/1992 |
| WO | WO 2006/082069 A1 | 8/2006 |

* cited by examiner

*Primary Examiner*—Terressa M Boykin
(74) *Attorney, Agent, or Firm*—Sutherland Asbill & Brennan LLP

(57) ABSTRACT

The invention relates to a method for continuously producing pre-ceramic polymers. The inventive method consists in synthesizing polymers, in separating polymers from a reaction mixture and in thermally conditioning for defining a cross linkage degree and rheological properties, wherein all said steps are integrated into a single method. The thus obtainable polymers are used in the form of an initial material for producing non-oxidized ceramics in ternary X/Y/N or X/Y/N/C quaternary systems. Said materials are characterized by the high mechanical, thermal and chemical resistance thereof, wherein any X and Y combination can represent in particular Si, B, P, Al, Ti, V, Zr, Ta elements.

19 Claims, 1 Drawing Sheet

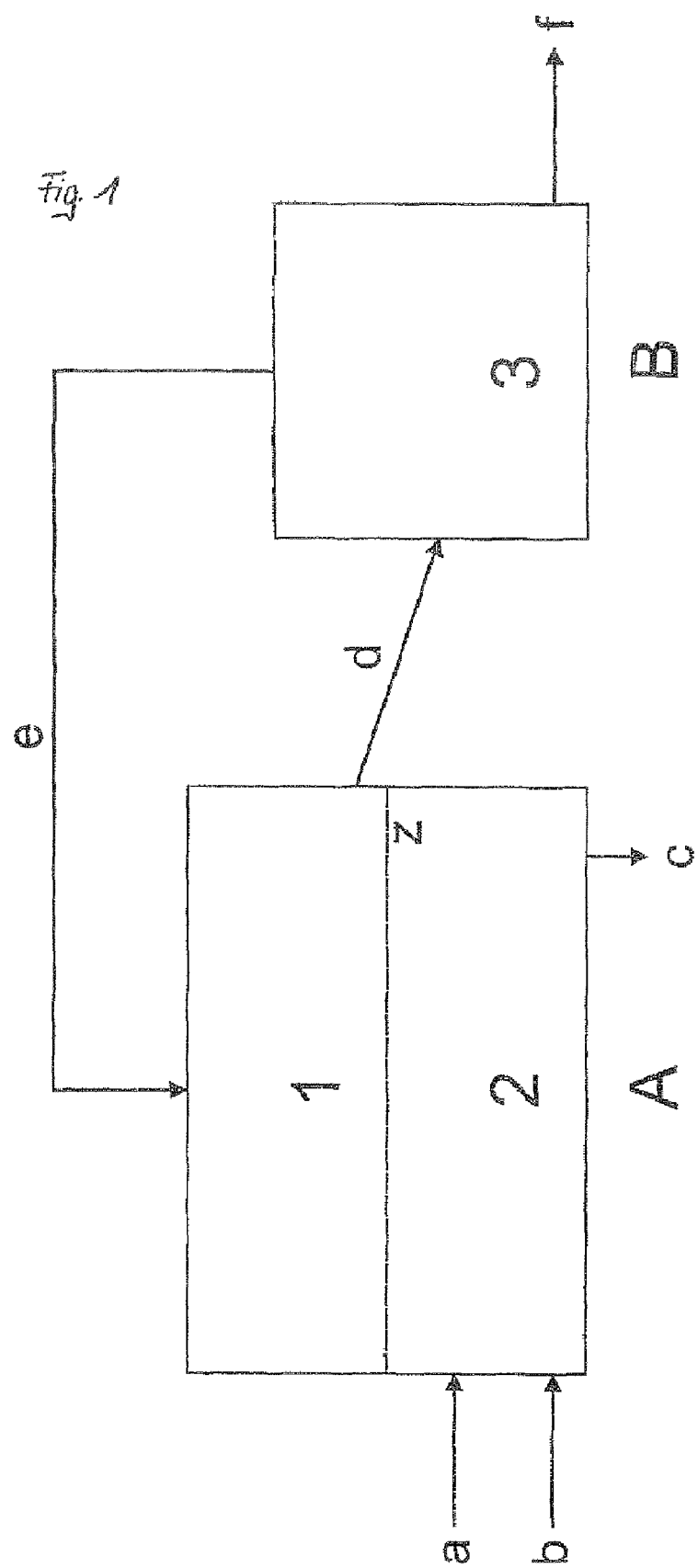

PROCESS FOR THE CONTINUOUS PREPARATION AND ISOLATION OF SOLUBLE PRECERAMIC OLIGOMERS AND/OR POLYMERS

CROSS REFERENCES TO RELATED APPLICATIONS

This application claims the priority benefit of PCT/EP2006/008745 filed on Sep. 7, 2006 and German Application No. 10 2005 042 813.4 filed on Sep. 8, 2005. The entire contents of these applications are hereby incorporated in their entirety.

BACKGROUND

Field of the Invention

The invention relates to a process for the continuous preparation of preceramic polymers. The process comprises the synthesis of the polymers, their separation from the reaction mixture and thermal conditioning to set the degree of crosslinking and the rheological properties in a single integrated process. The polymers prepared serve as starting materials for the production of nonoxidic ceramics in the ternary or quaternary system X/Y/N or X/Y/N/C. Such materials have a high thermal and mechanical stability and chemical resistance, and in them X and Y are any combinations of, inter alia, the elements Si, B, P, Al, Ti, V, Zr, Ta.

The preceramic polymers are prepared by crosslinking molecular precursors which in a preferred form contain the elements X and Y in a single molecule (one-component precursor). In a further embodiment, a mixture of various molecules which each contain an element X or Y can be crosslinked. The crosslinking of the precursor molecules is preferably effected by means of ammonia or a primary amine to form a preceramic polymer. The polymers can be processed to produce moldings, fibers, films or coatings and can finally be converted into the corresponding ceramic material at temperatures up to 1500° C.

Industrial processes by which polyborosilazanes have been produced from silicon- and boron-containing one-component precursors are described, inter alia, by Bayer AG in EP 0502399 A2. However, these processes of the prior art have a series of disadvantages from, inter alia, a technical point of view:

The crosslinking reagents ammonia and methylamine which are preferred for preparing the preceramic polymers are gaseous under normal conditions. The polymerization therefore has to be carried out either with cooling or under pressure.

The processes operate discontinuously. After polymerization is complete, at least three separate process steps are necessary to isolate the polymer:
vaporization of excess amine from the reaction mixture
filtration of the hydrochloride formed during the polymerization from the polymer and washing-out of the hydrochloride from adhering polymer
distillation of the solvent to isolate the polymer.

In a fourth process step which is additionally required, the degree of crosslinking required for further processing and the viscosity of the polymer or the molar mass are set (polycondensation step). Before this, the polymer has to be worked up and isolated completely.

Considerable amounts of organic solvents are required to separate the salt-like hydrochlorides from the polymer. This not only incurs high costs for the replacement or recovery of the solvent but also requires substantial safety measures for handling the solvents and in the disposal of the solvents.

It was an object of the present invention to provide a high-performance, continuously operating process which at least partly overcomes the abovementioned disadvantages of the prior art. In particular, the process should be able to be operated at ambient pressure and/or without cooling, i.e. under normal conditions. As a result, the engineering outlay for the construction of a corresponding plant can be considerably reduced and the operating costs can be decreased. In addition, the process should be applicable to the entire class of polymers specified at the outset.

SUMMARY OF THE INVENTION

According to the invention, this object is achieved according to the claims. Preferred embodiments are specified in the subordinate claims.

In particular, the invention provides a process for preparing preceramic polymers from molecular precursors for the synthesis of nitridic or carbonitridic ceramics, characterized in that
(a) the synthesis,
(b) the isolation and
(c) the conditioning of the polymers is carried out in a single contiguous production process.

The process of the invention encompasses a reaction system for the polymerization of molecular precursors with simultaneous extraction and isolation of the oligomers and/or polymers synthesized. The production process thus represents a contiguous or continuous process, i.e. separation of the process steps of synthesis/polymerization, isolation of the polymer and conditioning in either space or time is neither provided nor necessary.

The process of the invention can advantageously be carried out at atmospheric pressure and/or without cooling at ambient temperature, i.e. about 20° C. This means that the reactor according to the invention operates at ambient temperature and under atmospheric pressure.

A reaction mixture which can have one or more phases is present in the reactor. In a preferred embodiment of the process, the reaction mixture is liquid and consists of two phases during the polymerization. The reaction mixture comprises a solvent or solvent mixture, a molecular precursor (monomer) or a mixture of various molecular precursors, the crosslinking reagent, the oligomeric and/or polymeric product and the by-products formed during the course of the condensation reaction. When a crosslinking reagent which is gaseous under normal conditions, e.g. ammonia or methylamine, is used, this flows continuously through the reactor, dissolves partly or completely in the reaction mixture and reacts with the molecular precursor.

In the combined polymerization and extraction occurring in the reactor, preference is given to using two different, aprotic solvents of which one is nonpolar and one is polar. Examples of suitable nonpolar solvents are $C_5$-$C_{15}$-alkanes such as pentane, hexane, heptane, cyclohexane or aromatic hydrocarbons such as toluene, xylene, mesitylene or mixtures thereof. Examples of suitable polar solvents are chloroform, dichloromethane, tetrahydrofuran, acetonitrile, dimethylformamide, dimethyl sulfoxide, pyridine, imidazole, trimethylamine or mixtures thereof.

The solvents in their pure form can be completely miscible or have at least one miscibility gap. The two solvents should be selected so that a two-phase system is formed at least during the course of the polymerization under the respective reaction conditions.

In a preferred embodiment of the process, phase separation occurs as a result of one or more miscibility gaps between the pure polar and nonpolar solvents even before addition of the starting materials or phase separation occurs only after addition of the starting materials during the course of the polymerization.

In a particularly preferred embodiment of the process of the invention, a nonpolar aprotic solvent, for example $C_5$-$C_{15}$-alkanes such as pentane, hexane, heptane, cyclohexane or aromatic hydrocarbons such as toluene, xylene, mesitylene or mixtures thereof, and a polar aprotic solvent, for example chloroform, dichloromethane, tetrahydrofuran, acetonitrile, dimethylformamide, dimethyl sulfoxide, pyridine, imidazole, trimethylamine or mixtures thereof, are used.

Both the precursors and the crosslinking reagents can be fed to the reactor independently of one another, in pure or dissolved form.

Suitable crosslinking reagents are, for example, ammonia, methylamine, cyanamide, melamine, or it is possible to use a mixture of various crosslinking reagents, either stoichiometrically or in excess.

Crosslinking reagents which are gaseous under normal conditions (i.e. atmospheric pressure and ambient temperature), for example ammonia, methylamine or a mixture of ammonia and methylamine, are preferably dissolved in a solvent or a solvent mixture.

Suitable molecular precursors for the process of the invention are known to those skilled in the art and include the monomers used in previous processes of the prior art. The molecular precursors preferably have terminal chlorine atoms, hydrogen atoms or/and amino groups, with mixtures of appropriate monomers having different terminal groups also being able to be used.

Particularly suitable molecular precursors are, for example, trichlorosilylaminodichloroborane, methyldichlorosilylaminodichloroborane, dichloroborylmethyltrichlorosilylamine or trichlorosilyldichloroborylmethane or a mixture thereof.

In a preferred embodiment, the molecular precursor (or a mixture of various precursors) and the crosslinking reagent (or a mixture of various crosslinking reagents) are each fed into the reactor in pure form for the polymerization. As an alternative, the molecular precursor and/or the crosslinking reagent can firstly be dissolved separately in a suitable solvent in each case and then fed into the reactor for the polymerization. In another embodiment, the polymerization in the reactor is firstly carried out in a single phase in a suitable solvent and a two-phase mixture is then produced by addition of a second solvent.

The precursor (or a mixture of various precursors) to be crosslinked is continuously added to the solvent mixture present in the reactor and reacts there with the crosslinking reagent dissolved therein. If the precursor contains halogen atoms as leaving groups, salt-like by-products are formed by dehydrohalogenation reactions and dissolve in the polar solvent and increase its polarity further. If this polarity goes above a particular threshold value, phase separation into a polar solvent phase and a nonpolar solvent phase occurs if the mixture did not already consist of two phases before commencement of the polymerization reaction. Predominantly the polymer and the hydrochloride are dissolved in the polar phase, while virtually exclusively dissolved polymer is present in the nonpolar phase. The concentration of the polymer in the respective solvent phase is determined by the partition equilibrium of the polymer in these solvents. The polymer formed during the crosslinking reaction goes from the polar solvent phase into the nonpolar solvent phase at the phase boundary. A certain proportion of this polymer-containing solvent is continuously transferred via an overflow to an external collection vessel from where the nonpolar solvent is distilled off. The polymer remains and accumulates in the collection vessel, while the solvent which has been distilled off is recirculated to the reaction mixture. The circuit for the nonpolar solvent, which can be considered to be a carrier for the polymer, is thus closed. Accordingly, a constant amount of solvent which can be continuously circulated is required for the crosslinking of the molecular precursor and the separation of the polymer from the by-products.

Thus, part of the polymer formed during the course of crosslinking dissolves in the nonpolar solvent phase in a preferred embodiment.

The migration of the polymer from the polar solvent phase into the nonpolar solvent phase can be aided or accelerated by mechanical means, e.g. stirred apparatuses, or by external movements, in particular stirring movements.

Preference is given to both the molecular precursor and the crosslinking reagents being fed continuously into the reaction mixture at the rate or in the amount at/with which they are consumed.

Furthermore, the hydrochlorides formed during the course of the polymerization are preferably dissolved in the polar solvent phase, accumulate there and precipitate as solid when supersaturation is reached.

The setting of the degree of crosslinking of the polymer by self-condensation immediately after the synthesis represents a process step by means of which the rheological properties of the polymer can be controlled or directed. In the process of the invention, this conditioning can occur during the preparation of the polymer, since the polymer accumulating in the collection vessel during the extraction is permanently at the boiling point of the solvent. Thus, the degree of crosslinking of the polymer can advantageously be controlled or directed within wide limits both by the choice of the solvent used for the extraction, i.e. its boiling point, and via the time for which the polymer remains in the heated collection vessel before it is discharged from the production process.

In a preferred embodiment, part of the nonpolar, polymer-containing solvent phase is continuously branched off from the two-phase reaction mixture and transferred to an external collection vessel. Preference is also given to part of the nonpolar solvent being continuously distilled off from the collection vessel and recirculated to the reaction mixture. The polymer preferably accumulates in the collection vessel and partly precipitates out as solid.

In a further embodiment of the process of the invention, solids formed during the course of the production process, e.g. hydrochlorides or polymer, are discharged continuously from the production process. Furthermore, in one embodiment, the degree of crosslinking of the polymer can preferably be set via the boiling point of the nonpolar solvent. In a further embodiment, the degree of crosslinking of the polymer can be set via the residence time of the polymer in the collection vessel.

BRIEF DESCRIPTION OF THE DRAWINGS

The process of the present invention is illustrated by the accompanying drawing and the examples.

FIG. 1 shows the flow diagram of the continuous process of the invention in which synthesis, isolation and conditioning of the polymers are carried out in a single process.

DETAILED DESCRIPTION

The polymerization reactor (A) operates at room temperature and ambient pressure and contains the liquid phases (1) and (2). The volume ratio of these phases can in principle be chosen freely and is preferably in the range from 1:10 to 10:1. The upper phase (1) comprises a nonpolar aprotic solvent (e.g. $C_5$-$C_{15}$-alkanes such as pentane, hexane, heptane, cyclohexane or aromatic hydrocarbons such as toluene, xylene, mesitylene or mixtures thereof) in which the polymer formed during the polymerization dissolves. The lower phase (2) comprises a polar aprotic solvent (e.g. chloroform, dichloromethane, tetrahydrofuran, acetonitrile, dmethylformamide, dimethyl sulfoxide, pyridine, imidazole, triethylamine or mixtures thereof) and represents a good solvent for the crosslinking reagent used. The separation into two solvent phases with formation of the phase boundary (z) can be brought about by appropriate selection of two immiscible solvents. As an alternative, the nonpolar solvent and the polar solvent can also initially be completely miscible and separate only during the course of the polymerization as a result of the formation of a salt-like by-product which dissolves in the polar solvent. If the two solvents in their pure form are completely miscible, the phase separation can also be brought about by dissolution of salts (e.g. NaCl, methylamine hydrochloride, ammonium chloride) in the polar solvent component.

The molecular precursor (a) (e.g. trichlorosilylaminodichloroborane, methyldichlorosilylaminodichloroborane, dichloroborylmethyltrichlorosilylamine, trichlorosilyldichloroborylmethane or a mixture thereof) and the crosslinking reagent (b) (e.g. ammonia, methylamine, cyanamide, melamine or a mixture thereof) are fed continuously into the reactor. Here, the starting materials are preferably introduced into the polar solvent phase. The polymer formed during the course of the crosslinking reaction goes over from the polar (lower) solvent phase into the nonpolar (upper) phase at the phase boundary (z). This can be aided and accelerated by mechanical means such as stirred apparatuses or by means of external stirring movements. The polymer-enriched, nonpolar solvent phase goes via the overflow (d) into the external collection vessel (B) which is always above the boiling point of the nonpolar solvent. The solvent is permanently distilled off from there and recirculated to the reactor (e). The still relatively low molecular weight polymer synthesized in the reactor accumulates in the collection vessel and remains there at the boiling point of the solvent until the degree of crosslinking of the polymer has reached a particular value. If the degree of crosslinking increases further, the polymer precipitates, depending on temperature and concentration, as a solid and can be discharged from the production and extraction process (f).

The salt-like hydrochloride formed during the course of the polymerization accumulates in the polar solvent phase. There, it precipitates as a solid when its solubility product is exceeded and can, like the polymer, be continuously discharged from the process (c).

Example 1

Continuous preparation and isolation of a polyborosilazane by crosslinking of the one-component precursor $Cl_3Si$—$N(CH_3)$—$BCl_2$ (dichloroborylmethyltrichlorosilylamine, DMTA) by means of methylamine.

1000 ml of dichloromethane are mixed with 1000 ml of hexane. The monomer DMTA (0.5 g/min=2 mmol/min) and the crosslinking reagent methylamine (0.5 nl/min=22 mmol/min) are passed continuously into this homogeneous solution at room temperature and ambient pressure while stirring. During the course of this polymerization, a phase boundary is formed in the reaction mixture, with the upper phase comprising a solution of the polymer in hexane and the lower phase containing a proportion of the polymer and predominantly the by-product methylamine hydrochloride dissolved in dichloromethane. Part of the hexane/polymer solution goes via an overflow located directly below the surface of the liquid of the upper solvent phase into a collection vessel which is maintained at about 80° C. From there, part of the hexane distills back via the overflow, is condensed and recirculated to the two-phase dichloromethane/hexane mixture.

During the course of the production process, the polymer accumulates in the collection vessel and methylamine hydrochloride accumulates in the dichloromethane solvent phase. Both materials are continuously discharged from the production process via a solids separator.

Example 2

Continuous preparation and isolation of a polyborosilazane by crosslinking of the one-component precursor $C_{13}Si$—$NH$—$BCl_2$ (trichlorosilylaminodichloroborane, TADB) by means of methylamine.

1000 ml of acetonitrile are mixed with 1000 ml of hexane. The monomer TADB (0.5 g/min=2 mmol/min) and the crosslinking reagent methylamine (0.5 nl/min=22 mmol/min) are passed continuously into this homogeneous solution at room temperature and ambient pressure while stirring. During the course of this polymerization, a phase boundary is formed in the reaction mixture, with the upper phase comprising a solution of the polymer in hexane and the lower phase containing a proportion of the polymer and predominantly the by-product methylamine hydrochloride dissolved in acetonitrile. Part of the hexane/polymer solution goes via an overflow located directly below the surface of the liquid of the upper solvent phase into a collection vessel which is maintained at about 80° C. From there, part of the hexane distills back via the overflow, is condensed and recirculated to the two-phase acetonitrile/hexane mixture.

During the course of the production process, the polymer accumulates in the collection vessel and methylamine hydrochloride accumulates in the acetonitrile solvent phase. Both materials are continuously discharged from the production process via a solids separator.

The invention claimed is:

1. A process for preparing preceramic polymers from molecular precursors for the synthesis of nitridic or carbonitridic ceramics, wherein:
    (a) the synthesis,
    (b) the isolation; and
    (c) the conditioning of the polymers is carried out at ambient temperature and atmospheric pressure in a single contiguous production process wherein molecular precursors and crosslinking reagents are fed continuously into the reaction mixture at a rate at which they are consumed.

2. The process as claimed in claim 1, wherein it is carried out without cooling.

3. The process as claimed in claim 1, wherein all parts of the production process proceed continuously.

4. The process as claimed in claim 1, wherein the reaction mixture is liquid and consists of two phases during the polymerization.

5. The process as claimed in claim 4, wherein the phase separation occurs as a result of one or more miscibility gaps between the pure polar and nonpolar solvents even before addition of the starting materials or phase separation occurs only after addition of the starting materials during the course of the polymerization.

6. The process as claimed in claim 5, wherein a nonpolar aprotic solvent and a polar aprotic solvent are used.

7. The process as claimed in claim 1, wherein ammonia, methylamine, cyanamide, melamine or a mixture of various crosslinking reagents is used, either stoichiometrically or in excess.

8. The process as claimed in claim 7, wherein crosslinking reagents which are gaseous under normal conditions, in particular ammonia, methylamine or a mixture of ammonia and methylamine, are dissolved in a solvent or solvent mixture.

9. The process as claimed in claim 1, wherein molecular precursors which contain, independently of one another, chlorine atoms, hydrogen atoms, amino groups in terminal positions are used.

10. The process as claimed in claim 9, wherein trichlorosilylaminodichloroborane, methyldieblorosilylaminodichloroborane, dichloroborylmethyltrichlorosilylamine or trichiorosilyldichloroborylmethane or a mixture thereof is used as molecular precursor.

11. The process as claimed in claim 10, wherein part of the polymer formed during the course of crosslinking dissolves in the nonpolar solvent phase.

12. The process as claimed in claim 11, wherein the migration of the polymer from the polar solvent phase into the nonpolar solvent phase can be aided and accelerated by mechanical means such as stirred apparatuses or by means of external stirring movements.

13. The process as claimed in claim 12 wherein hydrochlorides formed during the course of the polymerization are dissolved in the polymer solvent phase, accumulate there and precipitate as solid when supersaturation is reached.

14. The process as claimed in claim 13, wherein part of the nonpolar, polymer-containing solvent phase is continuously branched off from the two-phase reaction mixture and transferred to an external collection vessel.

15. The process as claimed in claim 14, wherein part of the nonpolar solvent is continuously distilled off from the collection vessel and recirculated to the reaction mixture.

16. The process as claimed in claim 15, wherein the polymer accumulates in the collection vessel and partly precipitates as solid.

17. The process as claimed in claim 1, wherein solids formed during the course of the production process, e.g. hydrochlorides or polymer, are continuously discharged from the production process.

18. The process as claimed in claim 17, wherein the degree of crosslinking of the polymer can be set via the boiling point of the nonpolar solvent.

19. The process as claimed in claim 18, wherein the degree of crosslinking of the polymer can be set via the residence time of the polymer in the collection vessel.

* * * * *